(12) United States Patent
Lu et al.

(10) Patent No.: US 9,364,413 B2
(45) Date of Patent: Jun. 14, 2016

(54) METHOD FOR ANTI-AGING TREATMENT BY SURFACTIN IN COSMETICS VIA ENHANCING SIRTUIN

(71) Applicants: UMO International Co., Ltd., New Taipei (TW); Jenn-Kan Lu, New Taipei (TW)

(72) Inventors: Jenn-Kan Lu, New Taipei (TW); Hsin-Mei Wang, Pingtung (TW); Xuan-Rui Xu, New Taipei (TW)

(73) Assignees: UMO INTERNATIONAL CO., LTD., New Taipei (TW); Jenn-Kan Lu, New Taipei (TW)

( * ) Notice: Subject to any disclaimer, the term of this patent is extended or adjusted under 35 U.S.C. 154(b) by 1 day.

(21) Appl. No.: 14/448,401

(22) Filed: Jul. 31, 2014

(65) Prior Publication Data

US 2016/0030322 A1    Feb. 4, 2016

(51) Int. Cl.
| | |
|---|---|
| *A61K 8/64* | (2006.01) |
| *A61Q 19/08* | (2006.01) |
| *A61K 8/19* | (2006.01) |
| *A61K 8/63* | (2006.01) |
| *A61K 8/73* | (2006.01) |

(52) U.S. Cl.
CPC ... *A61K 8/64* (2013.01); *A61K 8/19* (2013.01); *A61K 8/63* (2013.01); *A61K 8/735* (2013.01); *A61Q 19/08* (2013.01); *A61K 2800/413* (2013.01); *A61K 2800/651* (2013.01); *A61K 2800/805* (2013.01)

(58) Field of Classification Search
CPC ....................................................... A61K 8/64
See application file for complete search history.

(56) References Cited

U.S. PATENT DOCUMENTS

| | | | |
|---|---|---|---|
| 2008/0311234 A1* | 12/2008 | Yoneda et al. | 424/780 |
| 2010/0168405 A1* | 7/2010 | Suzuki et al. | 536/4.1 |
| 2011/0212157 A1* | 9/2011 | Edelson et al. | 424/443 |
| 2012/0207700 A1* | 8/2012 | Koller et al. | 424/78.3 |

FOREIGN PATENT DOCUMENTS

WO    WO 2009/044279    *    4/2009    ............... C07K 7/64

OTHER PUBLICATIONS

Reddy et al., 2009, Synthesis of Gold Nanoparticles via an Environmentally Benign Route using a Biosurfactant, Journal of Nanoscience and Nanotechnology, 9: 6693-6699.*
Xu, "The application of surfactin for anti-aging cosmeceutical.", Department of Aquaculture Dissertations and Theses, http://ntour.ntou.edu.tw:8080/ir/handle/987654321/34598?locale=en-US, Oct. 7, 2013, 1 page.

* cited by examiner

*Primary Examiner* — Amber D Steele
(74) *Attorney, Agent, or Firm* — Muncy, Geissler, Olds & Lowe, P.C.

(57) ABSTRACT

Surfactin is a biosurfactant produced by *Bacillus subtilis* and is a natural cycloaliphatic peptide having a ring structure made of 7 amino acids. The surfactin has various functions including anti-aging, anti-wrinkle, increasing skin penetration of cosmetic products (skin penetration agent), foaming agent, and emulsifier.

17 Claims, 15 Drawing Sheets

SEQUENCE LISTING

```
<160> NUMBER OF SEQ ID NOS: 14

<210> SEQ ID NO 1
<211> LENGTH: 7
<212> TYPE: PRT
<213> ORGANISM: Bacillus subtilis

<400> SEQUENCE: 1

Glu Leu Leu Val Asp Leu Leu
1               5
```

<210> SEQ ID NO 2
<211> LENGTH: 24
<212> TYPE: DNA
<213> ORGANISM: Artificial sequence
<220> FEATURE:
<223> OTHER INFORMATION: Mouse RSP 16-F

<400> SEQUENCE: 2
ctgggtatct tgactaagcc tgac                                          24

<210> SEQ ID NO 3
<211> LENGTH: 24
<212> TYPE: DNA
<213> ORGANISM: Artificial sequence
<220> FEATURE:
<223> OTHER INFORMATION: Mouse RSP 16-R

<400> SEQUENCE: 3
agttctccac ctctttctca atcc                                          24

<210> SEQ ID NO 4
<211> LENGTH: 18
<212> TYPE: DNA
<213> ORGANISM: Artificial sequence
<220> FEATURE:
<223> OTHER INFORMATION: Mouse SIT1-F

<400> SEQUENCE: 4
tgtggctcca tcctacct                                                 18

<210> SEQ ID NO 5
<211> LENGTH: 18
<212> TYPE: DNA
<213> ORGANISM: Artificial sequence
<220> FEATURE:
<223> OTHER INFORMATION: Mouse SIT1-R

<400> SEQUENCE: 5
cattcctggg acgcttat                                                 18

<210> SEQ ID NO 6
<211> LENGTH: 21
<212> TYPE: DNA
<213> ORGANISM: Artificial sequence
<220> FEATURE:
<223> OTHER INFORMATION: Human-GAPDH-F

<400> SEQUENCE: 6
atgaggtgca tcgccctctt t                                             21

<210> SEQ ID NO 7
<211> LENGTH: 21
<212> TYPE: DNA
<213> ORGANISM: Artificial sequence
<220> FEATURE:
<223> OTHER INFORMATION: Human-GAPDH-R

<400> SEQUENCE: 7
tcaggcaaaa gctttctctc g                                             21

<210> SEQ ID NO 8
<211> LENGTH: 23
<212> TYPE: DNA
<213> ORGANISM: Artificial sequence
<220> FEATURE:
<223> OTHER INFORMATION: Human-SIT1-F

```
<400> SEQUENCE: 8
ggbgactact tggacatyct ggc                                              23

<210> SEQ ID NO 9
<211> LENGTH: 22
<212> TYPE: DNA
<213> ORGANISM: Artificial sequence
<220> FEATURE:
<223> OTHER INFORMATION: Human-SIT1-R

<400> SEQUENCE: 9
ttgctccaca catatttrcc rc                                               22

<210> SEQ ID NO 10
<211> LENGTH: 20
<212> TYPE: DNA
<213> ORGANISM: Artificial sequence
<220> FEATURE:
<223> OTHER INFORMATION: Human-SIT3-F

<400> SEQUENCE: 10
ggatttggac gtgcgaccaa                                                  20

<210> SEQ ID NO 11
<211> LENGTH: 20
<212> TYPE: DNA
<213> ORGANISM: Artificial sequence
<220> FEATURE:
<223> OTHER INFORMATION: Human-SIT3-R

<400> SEQUENCE: 11
cgtgtcagtg ctgtgtcgct                                                  20

<210> SEQ ID NO 12
<211> LENGTH: 20
<212> TYPE: DNA
<213> ORGANISM: Artificial sequence
<220> FEATURE:
<223> OTHER INFORMATION: T7

<400> SEQUENCE: 12
taatacgact cactataggg                                                  20

<210> SEQ ID NO 13
<211> LENGTH: 21
<212> TYPE: DNA
<213> ORGANISM: Artificial sequence
<220> FEATURE:
<223> OTHER INFORMATION: SP6*

<400> SEQUENCE: 13
atttaggtga cactatagaa t                                                21

<210> SEQ ID NO 14
<211> LENGTH: 18
<212> TYPE: DNA
<213> ORGANISM: Artificial sequence
<220> FEATURE:
<223> OTHER INFORMATION: Oligo d(T)*

<400> SEQUENCE: 14
tttttttttt tttttttt                                                    18
```

METHOD FOR ANTI-AGING TREATMENT BY SURFACTIN IN COSMETICS VIA ENHANCING SIRTUIN

BACKGROUND OF THE INVENTION

1. Field of the Invention

Present invention relates to the applications of surfactin, in particular, applications of surfactin in cosmetic products.

2. Description of the Prior Art

1. Human Skin Structure and its Aging Factors

Skin is the major organ on the surface in the human body and its thickness varies with the location, age, and gender. The main function of skin is to serve as the primary barrier to prevent damage to the internal organs by external environmental factors, e.g. UV light, temperature variations, humidity changes and particulate matter and viral or bacterial entry. Therefore, the aging mechanism can be easily triggered in the skin by external factors to replace damaged cells.

(1) Cellular Aging and Genetic Defects

Aging starts to take effect on cells followed by tissues and organs and results in structural as well as functional deterioration of some tissues and organs. The study conducted by Leonard Hayflick in 1963 found that the frozen cells isolated from human will undergo deformation after been passaged for a certain number of times, the. Base on the results, human cell exist a upper limit for cell division, and the rate of cell division and the appearance of the cells will change after 50 passages, resulting in irregular division and granular- or twisted abnormal cell appearances and eventually inducing apoptosis of the cells. This study suggested that the life cycle of an organism was determined at the stage of fertilization and the biological clock of an organism was pre-determined. In humans, cells can divide up to 50 times which is around 120 years. Because human cells do not express telomerase for replication of the lost sequences during DNA replication and consequently genes are damaged over the processes of multiple replications and divisions and thus creates a restriction on cell cycle and such restriction is called glass ceiling and this is an irreversible and inevitable aging process.

(2) Ultraviolet (UV) Light

The skin and other organs will age over time, but the skin aging is more serious when compared with other organs due to the effects of various environmental factors in daily life. Among numerous aging factors, ultraviolet (UV) irradiation is the most influential factor of all. The UV wavelength ranges from 10 to 400 nm with energy between 3 eV and 124 eV. UV light can be divided into three classes based on its wavelength: (1) long-wavelength UV-A, with a wavelength between 315 and 400 nm, can directly pass through the atmosphere and reach the surface. It also can penetrate the dermis layer of the skin and cause black spots, aging and wrinkles UV-A posses the strongest penetration capacity among the 3 wavelengths; (2) medium-wavelength UV-B, with a wavelength between 280 and 315 nm, will result in skin redness, heat, pain, and even peeling or burns-like symptoms. But UV-B will be absorbed by stratospheric ozone and only limited irradiation will reach the surface of the Earth; (3) short-wavelength UV-C, with a wavelength between 100 and 280 nm, is the highest energy and is harmful. However, its short wavelength will be absorbed by the atmosphere and thus only 0.1% can reach the surface of the Earth. Moreover, general shield and glass barrier can block UV-C rays effectively. Previous study reported that UV-A may induce synthesis of matrix metalloproteinases in human skin fibroblasts and the members of the matrix metalloproteinases family will degrade collagen, elastin and other substances in intracellular matrix and cause aging. In addition, UV-A may increase the level of free radicals in cells and excess free radicals will also lead to premature aging or even apoptosis.

(3) Free Radical

Free radical theory is the most accepted scientific theory of aging at present and is proposed by Dr. Denham Harmam M.D. at Lincoln University School of Medicine in 1954. But the theory was not accepted until 20 years later and now it has become one of the major theories of aging. Denham Harmam was nominated and awarded the Nobel Prize in Medicine in 1995. Normal atoms contain paired electrons, whereas free radicals contain oxygen with unpaired electrons. Because unpaired electrons are extremely unstable, free radicals will transfer the electrons from normal atoms and thus induce change in the intracellular matrix and result in cell death.

In addition to metabolism or synthesis of nutrients in vivo, important sources of free radicals which can lead to aging also include environmental pollution, ultraviolet light, radiation, smoke, pesticides, and many chemicals, particularly environmental pollution (automobile exhaust and SO2 emissions by factories) and all these may contribute to production of significant amount of free radicals in vivo.

Free radical attack can be divided into cell membrane damage and DNA damage. For human cells, oxygen-containing free radicals include superoxide anion $O_2$—, hydrogen peroxide $H_2O_2$, hydroxyl radical OH—, etc. and they are called reactive oxygen species (ROS). Excess free radicals will easily attack unsaturated fatty acids in cell membrane. When free radicals attack unsaturated fatty acids in cell membrane, lipid peroxidase will be produced and oxidize LDL cholesterol in vascular walls and inhibit the activity of prostacycline synthetase, resulting in atherosclerosis, diabetes, arthritis, cataracts, aging and coronary artery disease. If the free radical is deep down to the nucleus and altered genetic information, cancer may occur. In addition, free radicals can induce aging genes and promote aging. Studies have indicated that nearly 80%-90% of the aging and degenerative diseases are associated with free radicals, which include cancers, Alzheimer's disease, Parkinson's disease, muscular dystrophy, skin spot deposition, wrinkle formation, yellow spots, degenerative heart disease, stroke, ulcers, rheumatoid arthritis and multiple sclerosis.

Cellular defense mechanisms against free radicals: various antioxidant enzymes synthesized by the cells, e.g. enzymes glutathione Peroxidase (GPx) and superoxide Dismutase (SOD), and Glutathione (GSH), which can remove superoxide anions ($2O_2$—+$2H+H_2O_2+O_2$, $2GSH+H_2O_2$ and GS—SG+$2H_2O$) generated naturally in vivo. Studies have also suggested long-lived animals contain higher level of SOD in vivo and humans are the animals known by far that contain the highest level of SOD. Natural aging, physical changes and environmental factors can all cause insufficient production of antioxidants in vivo and result in aging.

(4) Inflammation

Inflammation is the response produced when the tissue is injured or infected. At first, the mast cells will arrive at the tissue and attach to the endothelial cells before releasing following substances:

(1) Histamine: a derivative of amino acid which can increase the permeability of capillaries and local vasodilation to allow substances such as plasma and macrophages to pass through and cause itching and allergic reactions.

(2) Tumor Necrosis Factor (TNF): cytokines will kill target cells and activate the immune system to induce proliferation of lymphocytes and prevent pathogen proliferation and also recruit macrophages to come to the site of infection.

(3) Prostaglandin: induce vasodilation of the capillaries and cause pain at the nerve ending. Pus will be produced following inflammation, which consists dead cells and body fluids and usually be digested by macrophages.

Specific cytokines will activate cyclooxygenase (COX), including COX-1 and COX-2. COX converts arachidonic acid into prostaglandins such as PGE 2 and PGF 2α. Recent studies have shown COX-2 is not found in most normal tissues, but it can be detected in patients with various cancers, indicating the importance of COX-2 in cancer patients. Additionally, COX-2 is an inducible enzyme whose function is to activate macrophages or other cells and exists in the inflammatory tissues.

The inflammatory sites will generate heat which is mainly due to releasing of angiotensin or histamine. Some cells will release the inflammatory cytokine IL-17 (Interleukin-1 alpha), formerly known as interleukin, to activate leukotriene to against allergens and the cytokines also include chemokines Said chemokines will initiate the chemoattractant mechanism and interferon and terminate protein synthesis in host cells. On the other hand, growth factors and cytotoxic molecules may also be released for healing of the tissues. Secretion of the abovementioned substances will affect the surrounding areas and cause loss of intracellular matrix and result in aging.

From the four aging factors mentioned above, during the process of skin aging, proliferation of the fibroblasts in epidermis and dermis layers will be decelerated which consequently contributes to changes of the large molecules and structural proteins in intracellular matrix of the dermis layer and result in symptoms of aging including skin folds, thinning of the skin, dull skin, reduced skin elasticity and moisture level. Alternatively, UV light induces production of intracellular proteases to break down collagen and elastic fibers in the skin tissue. Additionally, UV light may also increase the levels of free radicals in the cells and lead to premature aging due to skin inflammation. Moreover, the skin will generate ROS after UV light exposure that will destroy cellular structures such as cell membranes, structural proteins and nucleic acids and eventually result in cancerous development and death of the skin cells as well as wrinkles due to loss of intracellular matrix.

2. Human Anti-Aging Proteins

Some studies have indicated that under the stimulation of the chemical substance resveratrol in wines or restriction of calorie, the sirtuins family will be activated and extends the cell cycle, whereas Sinclair from the Leonard Guarente lab at MIT found that a special Sirtuins protein in yeast can affect the process of aging by using two specific approaches and Sirtuins can help regulate the gene activity of the cell and repair DNA breakage.

Philipp Oberdoerffer from the Sinclair lab, on the other hand, utilized microarrays of mouse cells to screen for the DNA sequence of mammalian sirtuin gene using the sirtuin gene from yeast, and the animal studies using mice also confirmed the yeast sirtuin-like gene exists in vertebrates as well. Oberdoerffer reported that the main function of Sirtuin in mammalian animals is to supervise the mode of gene expression. All genes will present in all cells; however, only limited genes need to be activated at specific time periods. If wrong genes were activated, cell damage will occur and induce apoptosis of the damaged cell.

Inhibited genes will undergo deacetylation induced by Sirtuins so as to protect the suppressed genes from damage resulting from environmental factors and ensure the suppressed genes remain shut down and safeguard the stability of the genes. Sirtuins can help preservation of chromatin and contract and cover the genes and histones and assure it remain idle. When the DNA is damaged by UV light or free radicals, Sirtuins will assist the repair mechanism at the damaged sites. Sirtuins covers the genes and proteins to exerts its protective function before permanent damage was resulted. Without the protection from Sirtuins, histones will start to relax the structure and the suppressed genes will be reactivated which makes the genes susceptible to external interferences and be damaged.

When the mice age, DNA damage rate will increase and this type of damage will lead to uncontrolled gene expression and relaxing of the chromatin. At the time, Sirtuins will help to control the deteriorated genome. Many of the genes activated during the loss-of-control process are the genes directly associated with the phenotypes of aging.

Other research suggested the mouse genes which were not controlled by Sirtuins will be continuously expressed in the aged mice. Oberdoerffer used a transgenic lymphoma mouse model to investigate the function of sirtuin and found that the average life span of the mice was extended 24%~46% if extra copies of the sirtuin gene was given or the mice was fed with the sirtuin activator, resveratrol.

Alternatively, study conducted by Leonard Guarente indicated utilization of new drugs rearranged the distribution of Sirtuins over time and new approach will be generated to protect the cells from aging. Based on this specific mechanism, though DNA damage may deteriorate the process of aging, this result is not due to DNA damage, but, is resulted from lack of gene regulation. Furthermore, Oberdoerffer's study also showed that this process of regulation of gene expression is called epigenetics which is different from the actual mutation of DNA. By validation of this principle, it is found that stimulation of Sirtuins can reverse the process of aging.

3. Transdermal Penetration Enhancers (TPE)

Studying of new drug requires significant amount of money and time and therefore development of drug delivery systems has attracted more attention over the years. The most common drug administration methods include oral administration, subcutaneous injection and transdermal administration. Oral administration is the most common method of administration and the drug enters bloodstream after being absorbed by gastrointestinal mucosa and exerts its effect either locally or systematically. Nonetheless, the disadvantages of oral administration include slow and irregular absorption in vivo which reduces the treatment effects. Moreover, the drug has to pass through the liver before arrive at the blood which not only reduces the therapeutic effects of the drug but also increases the burden on the liver. Certain drugs cannot be orally administered due to poor intestinal absorption or irritation, and the most serious drawback of oral administration is the side effects of the drug which may cause discomfort in patients such as nausea and vomiting. Another administration method is subcutaneous injection which directly inject the drug into the subcutaneous region to allow absorption by subcutaneous capillaries and delivery to the body. The advantage of this method is the drug is not affected by gastric juice and the liver and can enter blood vessels directly and pass through various body parts and achieve the therapeutic effect. The subcutaneous injection significantly increases the rate of administration when compared with oral administration. However, for patients requiring long-term injections, it is a burden to bear the pain caused by prolonged injection. The other administration method is using the transdermal drug delivery system (TDDS) and the drug is absorbed by the skin in this system. After administration, the drug will pass through stratum corneum at pre-determined time periods and be absorbed by capillaries before entering blood circulation and exert its effect so as to achieve the aim of systematic therapy (Saunders et al., 1999).

The advantages of transdermal drug delivery system (TDDS) include easy production, low cost, constant rate for delivery, maintain long-term stable concentration of drug, lower administration frequency, low toxicity, reduced hepatic first pass effect, reduced drug metabolism, less individual differences in drug use, increased bioavailability and the therapeutic effects can be achieved with low dose administration. In addition, TDDS is suitable for used in children, elderly or patients with problems of drug intake; can be easily applied and be removed immediately to stop administration when problems occur. Because TDDS has the abovementioned advantages, this system has attracted much attention. At present, research and development of the TDDS system has evolved from local to systematic, target organs and controlled release and has been applied in clinical use (Shin et al., 2005).

The major obstacle of TDDS system is the skin's stratum corneum. Stratum corneum (SC) is the top layer of skin and is composed of flat and long keratin cells and surrounded by layers of fat (Norlen, 2001). The major function of SC is to prevent entry of foreign substances and water loss and is the outermost barrier of the skin (Bouwstra et al., 2003). In 1973, Breathnach et al. discovered the intracellular space between the cells in SC is filled with fat which plays an important role in the skin barrier function (Breathnach et al., 1973). Similarly, other studies also suggested that the fluidity of the fat in the intracellular space in SC increases when the temperature of SC elevates and consequently percutaneous absorption of the skin increases accordingly (Golden et al., 1987). The hydrophilicity and skin permeability of the amphipathic drugs increase significantly if the fat was removed from the SC; however, removal of fat showed no significant effect on lipophilic drugs (Tsai et al., 2001).

Three methods are available to overcome the obstacle of percutaneous absorption: first, the physical method, provide extra energy to create transient holes in the skin to promote drug absorption and common treatments include ultrasound, iontophoresis, microneedle array and thermal energy. The second approach is a biochemical method of using the combination of biotransformation of precursors and metabolic inhibitors to increase absorption of drugs. The third method is a chemical method in which liposome is used to cover the drugs or a penetration enhancer is added. Liposome consists of curved lipid bilayer with the hydrophilic end extruding outside and hydrophobic end facing inside and can be used as a carrier for both hydrophilic and hydrophobic substances. Oily drugs can integrate into the lipid bilayer, whereas hydrophilic drugs can be covered in the water phase of the liposomes. The interaction between liposome and cells involves four mechanisms: intermembrane transfer in which part of the composition of liposome is exchanged with the composition of the cell membrane; adsorption in which liposomes adhere to the cell membrane; fusion in which liposomes fuse with the cell membrane and deliver the content into the cell; and finally, endocytosis in which liposomes are taken by the cell. The penetration enhancer refers to substances which can promote permeability and the amount of drugs absorbed by the skin but will not cause serious irritation and damage (Williams and Barry, 1991). The penetration enhancer mainly take effect in the intercellular layer of the SC and disrupts its regular structure and increases fluidity; moreover, it acts on keratin to lossen the structure of keratinocytes, increase the solubility of drugs in SC and enhance absorption of drugs (Walker and Smith, 1996). Addition of penetration enhancer is a very helpful method to increase skin permeability (Saunders et al., 1999).

Surfactants are excellent skin penetration enhancers and can aid in increasing the permeability of biofilm and the skin (Lopez et al., 2000) and have been widely applied in drug penetration recently (Nokhodchi et al., 2003; Shokri et al., 2001). In 2001, Nokhodchi et. al suggested surfactants sodium lauryl sulfate (SLS), cetyltrimethylammonium bromide (CTAB) and benzalkonium chloride can enhance skin absorption of the anti-depression drug Diazepam in mice (Shokri et al., 2001). Another study conducted by Nokhodchi et. al on anti-depression drugs also indicated surfactants sodium lauryl sulfate (SLS), cetyltrimethylammonium bromide (CTAB) and benzalkonium chloride can enhance skin absorption of lorazepam in mice (Nokhodchi et al., 2003). Surfactin exhibits great affinity for synthetic cell membranes, prokaryotic cell membranes and eukaryotic cell membranes (Maget-Dana and Ptak, 1995; Sheppard et al., 1991; Tsukagoshi et al., 1970b) and the binding between surfactin and cell membranes is highly selective which is due to surfactin has high affinity for cholesterol and phospholipid and these two structures are the major constituents of the cell membrane (Hosono and Suzuki, 1985). When compared with chemically synthesized surfactants, surfactin is more gentle and does not harm to the skin.

By conventional methods, drugs or nutritional active substances can only penetrate the barrier of epidermis (stratum corneum) and the exerted effects are not significant (up to 0.3% effectiveness). To solve this problem, a number of TDDS systems have been developed for the purpose of enhancing nutrient penetration so as to allow the nutrients to pass through epidermis and dermis layers of the skin and consequently nutrient delivery method has become the major research topic of skin care technology.

Although the stratum corneum of human skin is very thin, only 10-25 microns in thickness, and the thinnest SC is at the cuticle eyelids, 6 microns, the SC is rather "tough" and is the most important protective layer of the skin. Common cosmetics primarily penetrate the skin through 3 major pathways: 1. through sweat duct; 2. pas through stratum corneum directly; and 3. through hair follicle.

Using the cosmetic ingredient gold as an example, modern studies on gold beauty has confirmed that gold has the functions of detoxification, calm, clean and wrinkle reduction and can rearrange cellular factors, promote physiological functions and metabolism, balance oil/water secretion, retain natural water and prevent allergy caused by external factors. One the other hand, nanogold, a common ingredient used in cosmetic products has a size close to $1/200$ of a human pore and thus the purpose of using skin care products containing nanogold particles is to facilitate penetration of nanogold to the cells in deep dermis.

After entering the dermal layer, nanogold can regulate the function of dermal cells at the genetic level, including induce dermal cells to produce a series of active substances such as SOD, metallothionein and EGF. Because SOD can scavenge hydroxyl radicals, and metallothionein can help cortical cells to resist UV light damage, nanogold particles posses the anti-aging effect in dermal cells. Other studies also suggested nanogold can induce fibroblasts to secret and synthesize extracellular matrix (ECM) and to express and secret epidermal growth factor (EGF) in order to different target cell-specific keratinocyte growth factor (KGF) while strengthening the firmness of the skin and make the skin smooth and full of elasticity with shining glory.

4. Bioemulsifiers

In addition to be used as an anti-bacterial peptide, surfactin also plays another important role, bioemulsifier. Deleu et. al in 1999 discovered that ituirn A has better effect than surfactin in creaming-flocculation inhibition tests, while surfactin posses superior effect in emulsification of alkanes when compared with ituirn A and fengycin, and SDS was found to have the least effect in emulsification. Other research has shown that addition of 20 mg/l of surfactin can increase the biodegradability of diesel and further indicated pH value will affect the emulsification effect of surfactin on diesel and surfactin has the best biodegradability effect on diesel when the pH was adjusted to 7.4.

5. Foaming Agents

Besides the emulsification capability of common emulsifiers, surfactin also has the capacity to facilitate formation of foam (Razafindralambo et al., 1998). The foaming effect refers to surfactin exists between the gas and liquid phase and vigorous shaking allows surfactants to grasp the air and form a thin film containing air (Halling, 1981). Razafindralambo et. al also suggested surfactin presents better foaming effect when compared with ituirn A and speculated that the structures of these two agents are related to their foaming properties. Surfactin belongs to the anionic surfactants and its fatty acid carbon chain is shorter, while ituirn A is a non-ionic surfactant with a longer fatty acid chain (Razafindralambo, et al., 1998).

SUMMARY OF THE INVENTION

In one of the aspect, present invention provides a method for preparation of an anti-aging (or anti-wrinkle) cosmetic composition using surfactin; said composition is consisting of surfactin and pharmaceutically acceptable vehicles, excipients, diluents and adjuvants; wherein the surfactin is a cycloaliphatic hepapeptide consisting of 7 amino acids (L-Aspartic acid, L-leucine, glutamic acid, L-leucine, L-valine and two D-leucines) and this hepapeptide is linked to a β-hydroxy fatty acid which is mainly iso-C14 (17%~35%); and the distribution of the fatty acids at the fatty acid end of the surfactin are as follows: (1)iso-C13>3%; (2) C13>0.65%; (3) ios-C14>17%; (4) C14<41%; and (5) iso-C15<11%; wherein the preferred distribution of the fatty acids at the fatty acid end of the surfactin are as follows: (1) iso-C13>10%; (2) C13>25%; (3) iso-C14>35%; (4) C14<25%; and (5) iso-C15<3%; wherein the best distribution of the fatty acids at the fatty acid end of the surfactin are as follows: (1) iso-C13=11%; (2) C13=26%; (3) iso-C14=37%; (4) C14=24%; and (5) iso-C15=2%; wherein the molecular weight of the surfactin is 1022 or 1036 Da; wherein the surfactin comprises its isomers thereof. (See ROC Patent Application 097137532).

According to the invention, the anti-aging (anti-wrinkle) cosmetic composition can further comprises at least one of the following ingredients: alcohols, esters, complex polysaccharides, nut oils, and vitamins; wherein the alcohol comprises at least one of the following: C16-18 alcohols, butanediol, pentanediol, octanediol, glycerin, hexadecanol, stearyl alcohol, 1-Docosanol and propylene glycol; wherein the esters comprise at least one of the following: OLIVEM 1000, glycerol monostearate (GSM), isopropyl myristate (IPM), isopropyl palmitate (IPP) and triglycerides; wherein the complex polysaccharides comprise at least one of the following: xanthan gum, Tremella fuciformis polysaccharides, dextran polysaccharides, and Folium sennae seed polysaccharides; wherein the nut oil comprises at least one of the following: Argan oil, Kukui nut oil, avocado oil, wheat germ oil, and olive oil; wherein the vitamins comprise at least one of the following: vitamin A, vitamin B, vitamin C, vitamin E, vitamin F, and vitamin K.

According to the invention, the anti-aging (anti-wrinkle) cosmetic composition is used to induce fibroblast proliferation, resist UV light-induced aging, anti-oxidation, enhance the expression of sirtuin 1 gene, promote proliferation of collagen and inhibit the activity of matrix metallopeptidase; wherein the matrix metallopeptidase is matrix metallopeptidase 9.

In another aspect, present invention provides a method for preparation a composition to improve skin penetration by using surfactin, wherein the composition comprises surfactin and pharmaceutically acceptable vehicles, excipients, diluents and adjuvants; wherein the surfactin is a cycloaliphatic peptidecomprising 7 amino acids (L)Glu-(L)Leu-(D)Leu-(L)Val-(L)Asp-(D)Leu-(L)Leu linked to a β-hydroxy fatty acid and the distribution of the fatty acids at the fatty acid end of the surfactin are as follows: (1) iso-C13>3%; (2) C13>0.65%; (3) iso-C14>17%; (4) C14<41%; and (5) iso-C15<11%; wherein the preferred distribution of the fatty acids at the fatty acid end of the surfactin are as follows: (1) iso-C13>10%; (2) C13>25%; (3) iso-C14>35%; (4) C14<25%; and (5) iso-C15<3%; wherein the best distribution of the fatty acids at the fatty acid end of the surfactin are as follows: (1) iso-C13=11%; (2) C13=26%; (3) iso-C14=37%; (4) C14=24%; and (5) iso-C15=2%; wherein the molecular weight of the surfactin is 1022 or 1036 Da; wherein the surfactin comprises its isomers thereof; wherein the with enhanced skin penetration composition further comprises at least one of the following ingredients: alcohols, esters, complex polysaccharides, nut oils, and vitamins; wherein the alcohol comprises at least one of the following: C16-18 alcohols, butanediol, pentanediol, octanediol, glycerin, hexadecanol, stearyl alcohol, 1-Docosanol and propylene glycol; wherein the esters comprise at least one of the following: OLIVEM 1000, glycerol monostearate (GSM), isopropyl myristate (IPM), isopropyl palmitate (IPP) and triglycerides; wherein the complex polysaccharides comprise at least one of the following: xanthan gum, Tremella fuciformis polysaccharides, dextran polysaccharides, and Folium sennae seed polysaccharides; wherein the nut oil comprises at least one of the following: Argan oil, Kukui nut oil, avocado oil, wheat germ oil, and olive oil; wherein the vitamins comprise at least one of the following: vitamin A, vitamin B, vitamin C, vitamin E, vitamin F, and vitamin K.

According to the invention, the enhanced skin penetration composition is used to promote cosmetic ingredients to penetrate into the skin; wherein the cosmetic ingredients comprise dexamethasone, hyaluronic acid, Gamma-polyglutamic acid and gold-nanoparticles.

In the other aspect, present invention provides a method for preparation of an emulsifying composition using surfactin, wherein the emulsifying composition comprises surfactin and pharmaceutically acceptable vehicles, excipients, diluents and adjuvants; wherein the surfactin is a cycloaliphatic heptapeptide molecule comprising of 7 amino acids (L)Glu-(L)Leu-(D)Leu-(L)Val-(L)Asp-(D)Leu-(L)Leu linked to a β-hydroxy fatty acid and the distribution of the fatty acids at the fatty acid end of the surfactin are as follows: (1) iso-C13>3%; (2) C13>0.65%; (3) iso-C14>17%; (4) C14<41%; and (5) iso-C15<11%; wherein the preferred distribution of the fatty acids at the fatty acid end of the surfactin are as follows: (1) iso-C13>10%; (2) C13>25%; (3) iso-C14>35%; (4) C14<25%; and (5) iso-C15<3%; wherein the best distribution of the fatty acids at the fatty acid end of the surfactin are as follows: (1) iso-C13=11%; (2) C13=26%; (3) iso- C14=37%; (4) C14=24%; and (5) iso-C15=2%; wherein the molecular weight of the surfactin is 1022 or 1036 Da; wherein the surfactin comprises its isomers thereof; wherein the emulsifying composition further comprises of at least one of the following: glycerol fatty acid esters, sorbitan fatty acid esters, sucrose fatty acid esters, propylene glycol fatty acid esters, and lecithin.

According to the invention, the emulsifying composition is to increase the foaming power, increase emulsification, and increase smooth feeling; wherein the emulsifying composition is to increase the foaming power of detergents and said detergents are shampoo, face wash, hand wash cream and shower gel thereof; wherein the emulsifying composition is to increase the emulsification power of cosmetic products and said cosmetic products include body lotion, face cream, serums and blocking foundations thereof; wherein the emulsifying composition is to increase the smooth feeling of detergents and said detergents include shampoo, face wash, hand wash cream and shower gel thereof.

BRIEF DESCRIPTION OF THE DRAWINGS

FIG. 7(A)~(F) shows dexamethasone with 0, 0.2, 0.5, 1, 2, and 5% surfactin, respectively; SF: surfactin.

FIG. 8(A)~(F) shows HA with 0, 0.2, 0.5, 1, 2, and 5% surfactin, respectively; SF: surfactin.

FIG. 9(A)~(G) shows γ-GPA with 0%, 1%, 2%, 5%, 10%, 15% and 20% surfactin, respectively; SF: surfactin

DETAILED DESCRIPTION OF THE PREFERRED EMBODIMENT

Figure 1:
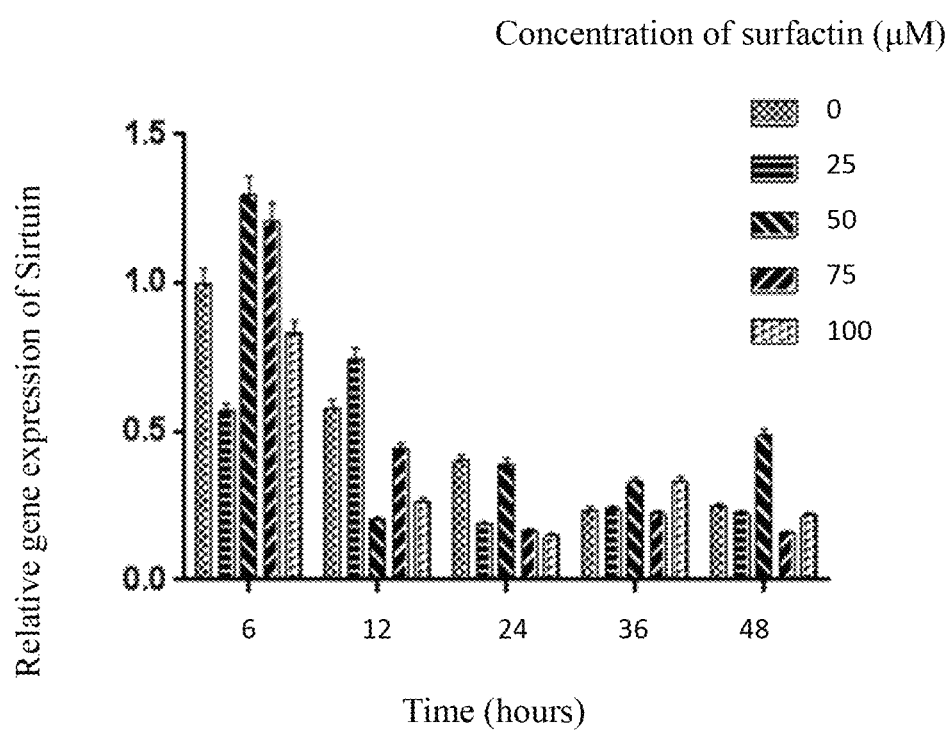
FIG. 1 shows the effect of different concentrations of surfactin on the mRNA expression of the long-lived gene sirtuin 1 in mouse embryo fibroblasts (BALB/3T3 clone A31 *Mus musculus* embryo fibroblast); mouse embryo fibroblasts were cultured with different concentrations of surfactin (0, 25, 50, 75 and 100 μM) for 6, 12, 24, 36 and 48 hours.

The present invention will now be described more specifically with reference to the following embodiments, which are provided for the purpose of demonstration rather than limitation. The following examples are illustrated using surfactin and said surfactin is a cycloaliphatic heptapeptide molecule comprising of 7 amino acids (L)Glu-(L)Leu-(D)Leu-(L)Val-(L)Asp-(D)Leu-(L)Leu linked to a β-hydroxy fatty acid (linked 13~15 hydrocarbon chain) and the iso-C14 of the fatty acid is around 37%.

EXAMPLE 1

Anti-Aging Effect of Surfactin on Human Skin and Mouse Embryo Fibroblasts

Materials and Methods

1. Cell Lines

Human skin fibroblast (CCD-966SK) was purchased from BCRC and the No. 60153

2. Mouse BALB/3T3 embryo (BALB/3T3 Clone A31) was purchased from BCRC and the No. 60009.

3. Animals

Single-sex BALB/cByJNarl mice weighing 200~250 g were purchased from National Laboratory Animal Center (Taiwan). Throughout the experiment, the mice were housed in air-conditioned (humidity at 75%) and temperature-adjusted (25° C.) cages with a 12-h light/dark cycle and free access to water and food at the Animal House of Department of Life Science, Ocean University.

4. Expression of the Anti-Aging Genes (1) cDNA Sequence Cloning of Human and Mouse Genes Total RNA was extracted from human skin fibroblasts and mouse embryo fibroblasts using TRIzol reagent (Invitrogen, USA), analyzed by RNA gel electrophoresis and subjected to RT-PCR for amplification of human skin fibroblasts sirtuin 1 and sirtuin 3 and mouse embryo fibroblasts sirtuin 1. GeneBan was used to identify well known sequences of sirtuins and GCG program was utilized to search for sequences with high similarity. A primer set was designed for polymerase chain reaction (PCR), followed by 1.2% agarose gel electrophoresis of a small portion of the reaction product to confirm the expected product has been amplified. Once confirmed, the remaining product was subjected to low-melting point agar gel electrophoresis, the product was excised from the gel and the specific size of DNA fragment was purified by gel extraction for cloning. The purified DNA fragment was ligated with the cloning vector pGEM-T-easy vector (pGEM-T-easy cloning kit, Promega, USA) before transformed into the competent cells. Finally, after small scale culture, cloning vector was extracted for sequencing, and the sequence data was compared using the BLAST program of NCBI. Part of the human skin fibroblast sirtuin 1 and sirtuin 3 and mouse embryo fibroblasts sirtuin 1 were correctly cloned by the abovementioned cloning procedures and the selected clones were transformed into competent cells again for extraction of plasmid with high purity for future experiments.

(2) Extraction of Cellular Total RNA

RNA is easily degraded in natural environment by RNase and thus all tools used must be autoclaved and dried in an oven prior to conducting experiments and wear gloves and masks during the procedures. Quickly add 800 µL TRIzol™ reagent to the culture dish of the experimental group and transfer the washed off cells to a sterile tube. Add chloroform to the tube in the volume of ⅕ of the total volume of TRIzol™ reagent and shake vigorously for 30 seconds. After incubation at room temperature for 15 minutes, centrifuge at 13200 rpm for 15 minutes at 4° C. and transfer the supernatant to a new 1.5 mL eppendorf. RNA is present in the aqueous phase of the supernatant. Transfer the supernatant to another clean 1.5 mL eppendorf and add Isopropanol in the volume of ½ of TRIzol™ reagent and high salt solution (1.2 M Sodium Chloride and 0.8 M Sodium citrate), mix well and incubate at −20° C. for 30 minutes, followed by centrifugation at 13200 rpm for 15 minutes at 4° C. to precipitate RNA; remove the supernatant carefully and add 800 µL of 100% absolute ethanol to wash and centrifuge at 13200 rpm for 10 minutes at 4° C. before washing with 100% ethanol. Carefully remove the supernatant and dry the RNA precipitate at 55° C. for 5 minutes. Dissolve the RNA precipitate in 15 µL DEPC water and incubate at 55° C. for 10 minutes and store at −80° C. freezer for future use.

(3) Measurement of the Concentration and Purity of RNA

Spectrophotometer was used to measure $OD_{260}$ and calculate the concentration of RNA, 1 $OD_{260}$=40 µg of RNA/mL and 40 µg×dilute factor×A260=µg/mL. The purity of RNA is determined based on the ratio of $OD_{260}/OD_{280}$, a number between 1.9 and 2.0 indicates high-purity RNA.

(4) Reverse Transcription (RT)

Place 5 µg of total RNA in a 200 µL eppendorf and adjust the volume to 13 µL with DEPC water, add 1 µL of oligo(dT) 18, 10 mM dNTPs and incubate on ice. Add 4 µl of 5×AMV buffer and 1 µl of AMV (40 units/µL) and mix well. Synthesize cDNA at 42° C. for 60, followed by incubation at 70° C. for 10 minutes to terminate the reaction.

(5) Polymerase Chain Reaction (PCR)

Amplify the cDNA template obtained from RT by polymerase chain reaction (PCR) using Taq polymerase. Mix 1 µL of cDNA with 0.5 µL of 10 mM dNTPs, 2.5 µl of 10×PCR buffer, Gene specific primer (GSP) (0.5 µL each), 0.25 µL of Taq polymerase and adjust the volume to 25 µL with sterilized water. Place the reaction tube in a PCR machine (DNA thermal cycler; Applied Biosystems 2720 Thermal Cycler) and amplify with the following conditions: 94° C. initial denaturation for 2 minutes; 94° C. denaturation for 30 seconds; 64° C. annealing for 30 seconds; 72° C. extension for 1 minute for a total of 30 cycles and store at 4° C. Take 5~15 µL of the PCR product and analyze by 1.5% agarose gel electrophoresis, stain with EtBr for 10 minutes and de-stain in water for 10 minutes. Check the image using the Digital Gel Image System and capture the photo by UN-SCAN-IT gel—Gel Analysis Software Version 6.1 Quantitative Analysis (6) Real-Time Quantitative (PCR)

The fluorescent dye SYBR green I can be embedded in the groove of double-stranded DNA and generate fluorescence when excited by a halogen light and its intensity can then be measured. When SYBR green I is not embedded in the groove of double-stranded DNA, its fluorescence background value is very low; and when it starts to integrate into the amplified target gene sequence, the fluorescence signal of SYBR green I will also be increased accordingly. In the absence of binding to non-specific primers or without contamination of genomic DNA, the PCR process can be divided into (1) geometric phase during which the amplification product is synthesized exponentially; (2) linear phase when the reactants are insufficient and the product is not synthesized exponentially and (3) the final plateau phase when all reactants are consumed and not effective. Therefore, to measure the expression level of the target gene in tissue organs, only quantification during the exponential phase of PCR can provide accurate data. The principle of real-time quantitative PCR is that under the same PCR conditions and in the presence of different templates concentrations, the templates at higher concentrations will reach the exponential phase faster than templates at relatively low concentrations, and the cycle number at which the signal of the reaction crosses the threshold is defined as CT (threshold cycle), literally, the CT value increases as the template concentration decreases. Standards at different concentrations are used to quantify the CT value of the PCR reaction in real time and the standard curve and regression equation were plotted using specific software and calculate the absolute level of gene expression in the test sample by interpolation. If the melting Curve is also desired, continuous fluorescence detection at the melting temperature 40° C.-99° C. can be performed following amplification cycle of the target gene and analysis of the melting curve allows understanding of whether primer self-complementary (primer-dimers) exists or the specificity of the primers and assists in assessing the quantitative accuracy.

Place the 96 well PCR plate in the freezer box which was designated for the 96 well PCR plate and pre-cooled at 4° C., and add 10 μL of SYBR green, 4 μL of each Real-time PCR specific primers (Table 1), 2 μL of RT product as the template for PCR reactions and sealed with a 96 well PCR plate film, followed by centrifugation at 1500 rpm for 3 minutes at 4° C. The sample will be at the bottom of the PCR plate. Place the PCR plate in the real-time PCR machine (Roche lightcycler 480 Real time PCR) and set the following conditions: hot start at 95° C. for 5 min; amplification at 95° C. for 30 seconds and annealing at 60° C. for 30 seconds for a total of 40 cycles and measure the fluorescence continuously to determine whether the amplified products are all at the same denaturation temperature. Analyze the data using Roche software after completion of the reaction. The data obtained from the experiment was analyzed with SPSS software, one-way analysis of variance and the significant difference was compared based on Duncan's Multiple Range Test (p<0.05). The resulted data is represented as Mean±SD.

trations has different effect on expression of the sirtuin 1 gene in mouse embryo fibroblast; after treating with surfactin for 6 hours, 50 μM and 75 μM of surfactin both enhance expression of the sirtuin 1 gene in mouse embryo fibroblasts; after treating with surfactin for 12 hours, 25 μM of surfactin shows enhancement of expression of the sirtuin 1 gene in mouse embryo fibroblasts; after treating with surfactin for 36 hours, 50 μM and 100 μM of surfactin both show enhancement of expression of the sirtuin 1 gene in mouse embryo fibroblasts; after treating with surfactin for 48 hours, 50 μM of surfactin shows enhancement of expression of the sirtuin 1 gene in mouse embryo fibroblasts, and among which 50 μM of surfactin demonstrates the best effect in enhancement of sirtuin 1 expression.

Figure 2:
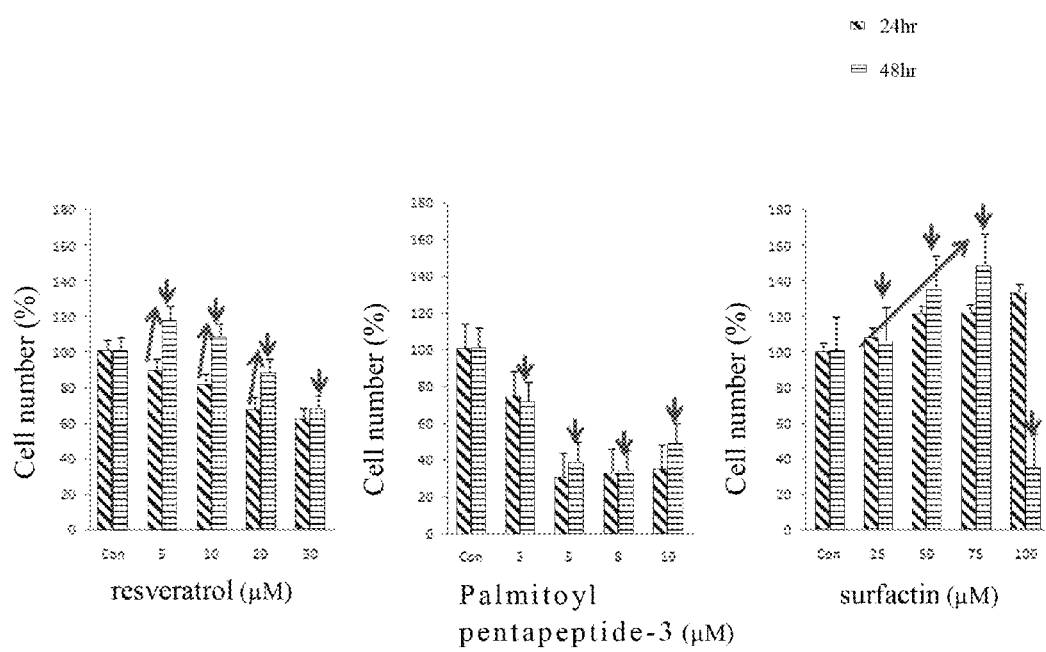
FIG. 2 shows the effects of resveratrol, palmitoyl pentapeptide-3 and surfactin on cell proliferation; mouse embryo fibroblasts were cultured with different concentrations of surfactin (0, 25, 50, 75 and 100 μM), resveratrol (0, 5, 10, 20 and 30 μM) and Palmitoyl pentapeptide-3 (0, 3, 5, 8 and 10 μM) for 48 hours.

FIG. 2 shows the effects of Resveratrol, Palmitoyl pentapeptide-3 and surfactin on mouse embryo fibroblast proliferation and the results indicates surfactin can enhance mouse embryo fibroblast proliferation; moreover, 75 μM of surfactin has the best effect in inducing cell proliferation, followed by 50 μM of surfactin. In addition, surfactin has better effect in inducing cell proliferation when compared with resveratrol and Palmitoyl pentapeptide-3.

TABLE 1

Real-time PCR specific primers

| | Primer | Sequence | Base |
|---|---|---|---|
| SEQ ID NO. 2 | Mouse-RSP16-F | 5'-CTG GGT ATC T TG ACT AAG CC T GAC-3' | 24 |
| SEQ ID NO. 3 | Mouse-RSP16-R | 5' AGT TCT CCA C CT CTT TCT CAA TCC-3' | 24 |
| SEQ ID NO. 4 | Mouse-SIT1-F | 5' TGT GGC TCC ATC CTA CCT-3' | 18 |
| SEQ ID NO. 5 | Mouse-SIT1-R | 5'-CAT TCC TGG GAC GCT TAT-3' | 18 |
| SEQ ID NO. 6 | Human-GADPH-F | 5'-ATG AGG TGC ATC GCC CTC TTT-3' | 21 |
| SEQ ID NO. 7 | Human-GAPDH-R | 5'-TCA GGC AAA AGC TTT CTC TCG-3' | 21 |
| SEQ ID NO. 8 | Human-SIT1-F | 5'-GGB GAC TAC TTG GAC ATY CTG GC-3' | 23 |
| SEQ ID NO. 9 | Human-SIT1-R | 5'-TTG CTC CAC ACA TAT TTR CCR C-3' | 22 |
| SEQ ID NO. 10 | Human-SIT3-F | 5'-GGA TTT GGA CGT GCG ACC AA-3' | 20 |
| SEQ ID NO. 11 | Human-SIT3-R | 5'-CGT GTC AGT GCT GTG TCG CT-3' | 20 |
| SEQ ID NO. 12 | T7 | 5'-TAA TAC GAC TCA CTA TAG GG-3' | 20 |
| SEQ ID NO. 13 | SP6* | 5'-ATT TAG GTG ACA CTA TAG AAT-3' | 21 |
| SEQ ID NO. 14 | Oligo d(T)* | 5'-TTT TTT TTT TTT TTT TTT-3' | 18 |

*: reverse primer

Primers in Table 1 are numbered in provided sequence list as the following;

Mouse RSP SEQ ID NO:2; Mouse RSP 16-R; SEQ ID NO:3; Mouse SIT1-F; SEQ ID NO:4; Mouse SIT1-R: SEQ ID NO:5; Human-GAPDH-F: SEQ ID NO:6; Human-GAPDH-R: SEQ ID NO:7; Human-SIT1-F: SEQ NO:8; Human-SIT1-R: SEQ ID NO:9; Human-SIT3-F: SEQ ID NO:10; Human-SIT3-R: SEQ ID NO:11; T7: SEQ ID NO:12; SP6*: SEQ ID NO:13; Oligo d(T)*: SEQ ID NO:14.

Results

Surfactin Enhances the Expression and Proliferation of the Long-Lived Sirtuin 1 Gene in Mouse Embryo Fibroblasts From FIG. 1, surfactin can promote the expression of the long-lived gene, sirtuin 1, in mouse embryo fibroblasts. When given different concentrations of surfactin, different concen-

EXAMPLE 2

Surfactin has the Effects of Anti-Photoaging and Anti-Oxidation

1. Surfactin has Anti-Photoaging Repairing Function

Following subculture of the mouse embryo fibroblasts and incubation for 4 hours for attachment, the cells were irradiated by UV-A at energy densities of 0 J/cm$^2$, 10 J/cm$^2$ and 15 J/cm$^2$ in a UV light hybridization box, followed by addition of 25, 50, 75, 100 and 125 μM of surfactin. After incubation for 24 hours, cell survival rates were measured by the MTT method.

Figure 3:
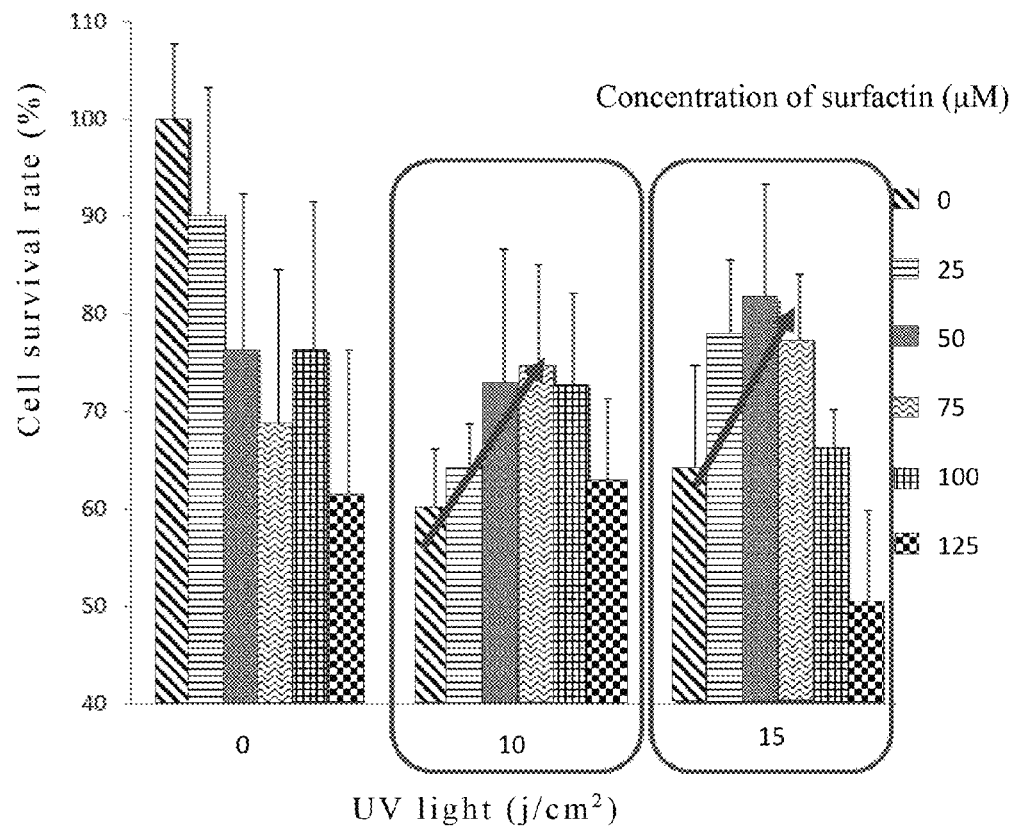
FIG. 3 shows the effects of surfactin on anti-photoaging; the effects of different concentrations of surfactin on survival of mouse embryo fibroblasts following UV irradiation; cells were irradiated with 5 J/cm2, 10 J/cm2 and 15 J/cm2UV light, followed by addition of 25, 50, 75, 100 and 125 μM of surfactin, incubation for 24 hours, and cell survival was measured by the MTT method.

From FIG. 3, surfactin has anti-photoaging repairing function. After irradiation by UV light at the energy density of 10

J/cm², 25, 50, 75, 100 and 125 μM of surfactin can all increase cell survival rate and among which the concentration of 75 μM shows the best protection. Moreover, after irradiation by UV light at the energy density of 15 J/cm², 25, 50, 75, 100 and 125 μM of surfactin can all increase cell survival rate and among which the concentration of 50 μM shows the best protection.

2. Surfactin has the Anti-Oxidation Repairing Function

Following subculture of the mouse embryo fibroblasts and incubation for 4 hours for attachment, hydrogen peroxide was used to treat the cells as the source of oxidation. The cells were treated with 100, 150, 200 and 25004 of hydrogen peroxide before addition of 25, 50, 75 and 100 μM of surfactin for another 24 hours. Cell survival rate was measured by the MTT method.

Figure 4:
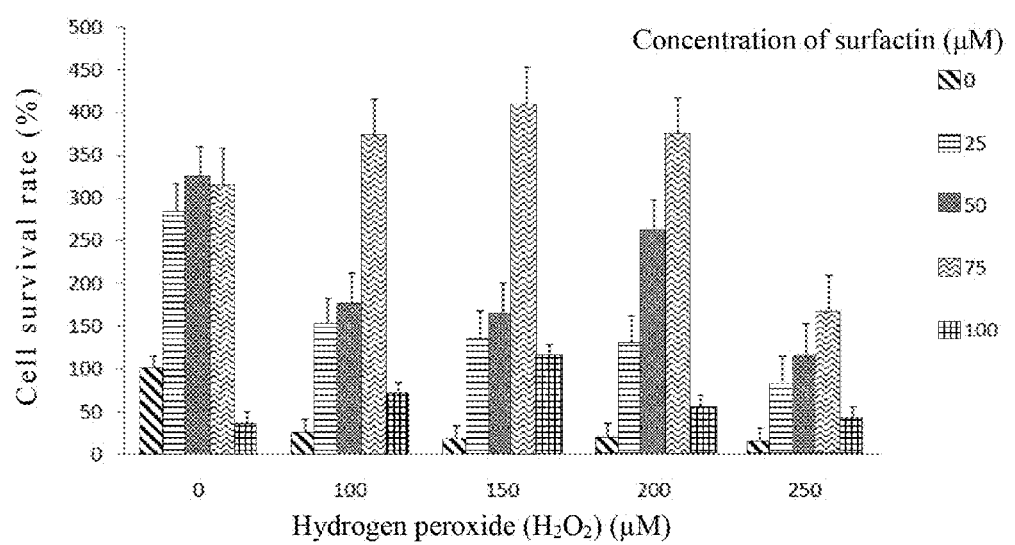
FIG. 4 shows the protective anti-oxidation effect of surfactin on mouse embryo fibroblasts; cells were treated with 100, 150, 200 and 250 μM of hydrogen peroxide, followed by addition of 0, 25, 50, 75 and 100 μM of surfactin, followed by incubation for 24 hours and cell survival was measured by the MTT method.

From FIG. 4, surfactin can increase the survival rate of mouse embryo fibroblasts treated with hydrogen peroxide, and 25, 50 and 75 μM of surfactin all have good protective effect and among which 7504 shows the most significant protection.

EXAMPLE 3

Surfactin Induces Production of Collagen in Mouse Embryo Fibroblasts

1. Analysis of the Concentration of Collagen

Sircol™ soluble collagen assay kit was used for analysis the total concentration of collagen in the culture media and the general method is described as follows:

Place 0.1 ml of the test samples and the standards at different concentrations in separate 1.5 mL centrifuge tubes. Add 1 mL of dye reagent and vortex for 35 minutes, followed by centrifugation at 12000 rpm for 10 minutes and remove the supernatant. Carefully remove the residue water at the side of the tube to avoid contact with the precipitate. Add 1 mL of Alkali reagent to dissolve the precipitate and transfer 0.2 mL to a 96-well pate after the color has developed and measure absorbance at 570 nm using an ELISA reader.

Figure 5:
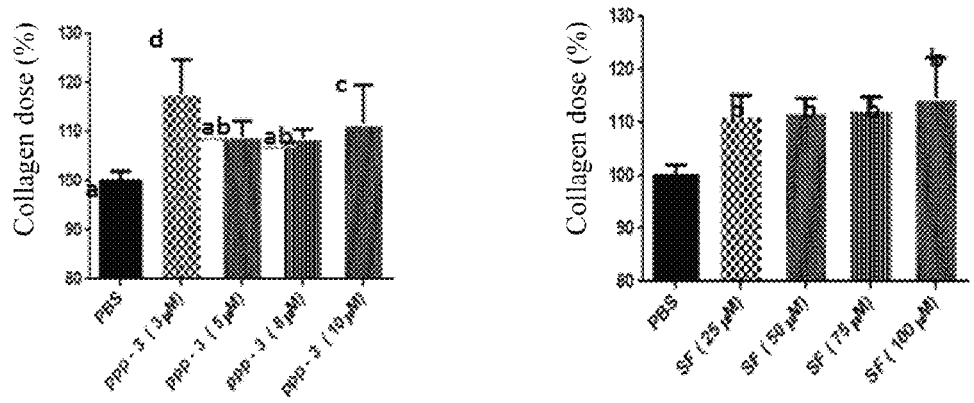
FIG. 5 shows the effects of surfactin and Palmitoyl pentapeptide-3 on collagen dose in mouse embryo fibroblasts; wherein the collagen dose is measured by Sircol collagen assay; mouse embryo fibroblasts were cultured with different concentrations of surfactin (0, 25, 50, 75 and 100 μM) and Palmitoyl pentapeptide-3 (0, 3, 5, 8 and 10 μM) for 24 hours; PBS: phosphate buffered saline; a, b, ab, c, and d: same symbols indicate no statistical differences.
Figure 6:
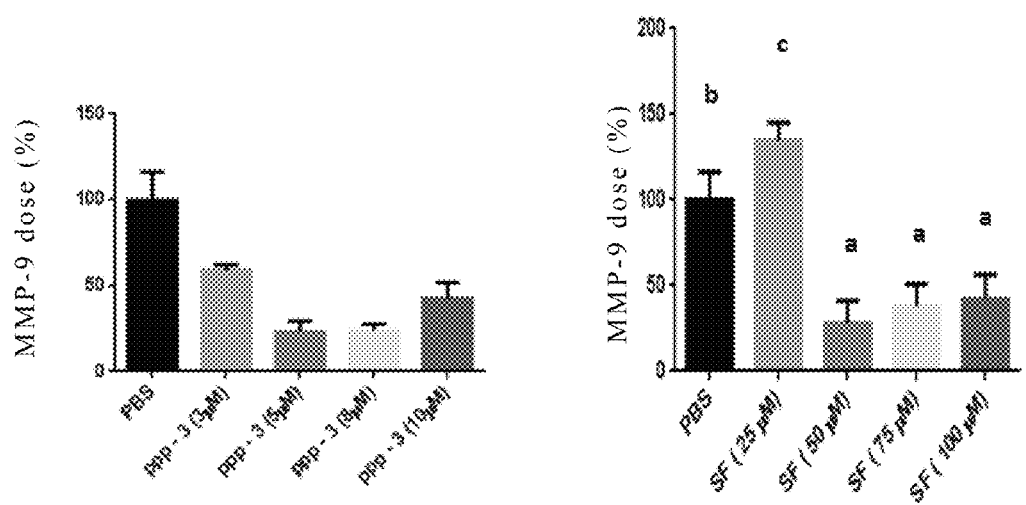
FIG. 6 shows the inhibition effect of surfactin (SF) and palmitoyl pentapeptide-3 (PPP-3) on matrix metallopeptidase 9; the concentration of matrix metallopeptidase was measured by ELISA; mouse embryo fibroblasts were cultured with different concentrations of PPP-3 (0, 3, 5, 8 and 10 μM) and surfactin (0, 25, 50, 75 and 100 μM); a, b, c: same symbols indicate no statistical differences.

2. Surfactin can Increase the Collagen Concentration in Mouse Embryo Fibroblasts From FIG. 5, surfactin can induce collagen proliferation in mouse embryo fibroblasts. When compared with cells cultured with phosphate buffered saline (PBS) of the control group, surfactin at the concentrations of 25, 50, 75 and 100 μM all have great effects in increasing collagen proliferation and among which the concentration of 100 μM shows the best result. Alternatively, though palmitoyl pentapeptide-3 (PPP-3) can also increase collagen content in the cells, its effect seems not as good as surfactin when compare with the results of surfactin.

EXAMPLE 4

Surfactin Inhibits the Activity of Matrix Metallopeptidase 9

1. Inhibition of Matrix Metallopeptidase 9

Following subculture the mouse embryo fibroblasts, commercial active anti-wrinkle substances 3, 5, and 10 μM Palmitoyl pentapeptide-3 were added and compared with the cells incubated with 25, 50, 75 and 100 μM of surfactin. Abnova MMP-9 (Mouse) ELISA Kit and ELISA Reader were utilized for analysis of the concentration of matrix metallopeptidase 9 in the cells.

2. Surfactin can Inhibit the Activity of Matrix Metallopeptidase

From FIG. 6, 50, 75 and 100 μM of surfactin can all inhibit the activity of matrix metallopeptidase and among which 50 μM of surfactin shows the best inhibition effect.

EXAMPLE 5

Surfactin Enhances Skin Penetration of Cosmetic Products

1. Experimental Methods

Before the experiment, the back of the mice was shaved. Mice aged 6-8 weeks were anesthetized by intraperitoneal injection using (Zoletil) and lay the animal flat before shaving the back with a electric razor and remove the remaining hair with hair removal cream. Place the animals in the cages with a warming light and provide water in each cage. Two groups are include in the experiment: for the control group, 100 μl of PBS (pH=7.4) was mixed with fluorescein isothiocyanate (FITC)-labeled HA or dexamethasone before added to 1 cm2 sterile cotton and affixed to the back of the mice; for the experimental group, FITC-labeled HA or dexamethasone was mixed with 0, 0.2, 0.5, 1, 2 and 5% surfactin for 1 hour.

At the end of 1 hour treatment, sacrificed the mice with CO2 asphyxiation, clean up the drug residue on the skin with ethanol and cut the skin on the back and embedded in Optimum cutting temperature compound (O.C.T) (SAKURA®, Japen) for cryosection (CM-2000, Leica, Germany).

2. Surfactin Enhances Skin Penetration of Dexamethasone

Figure 7:
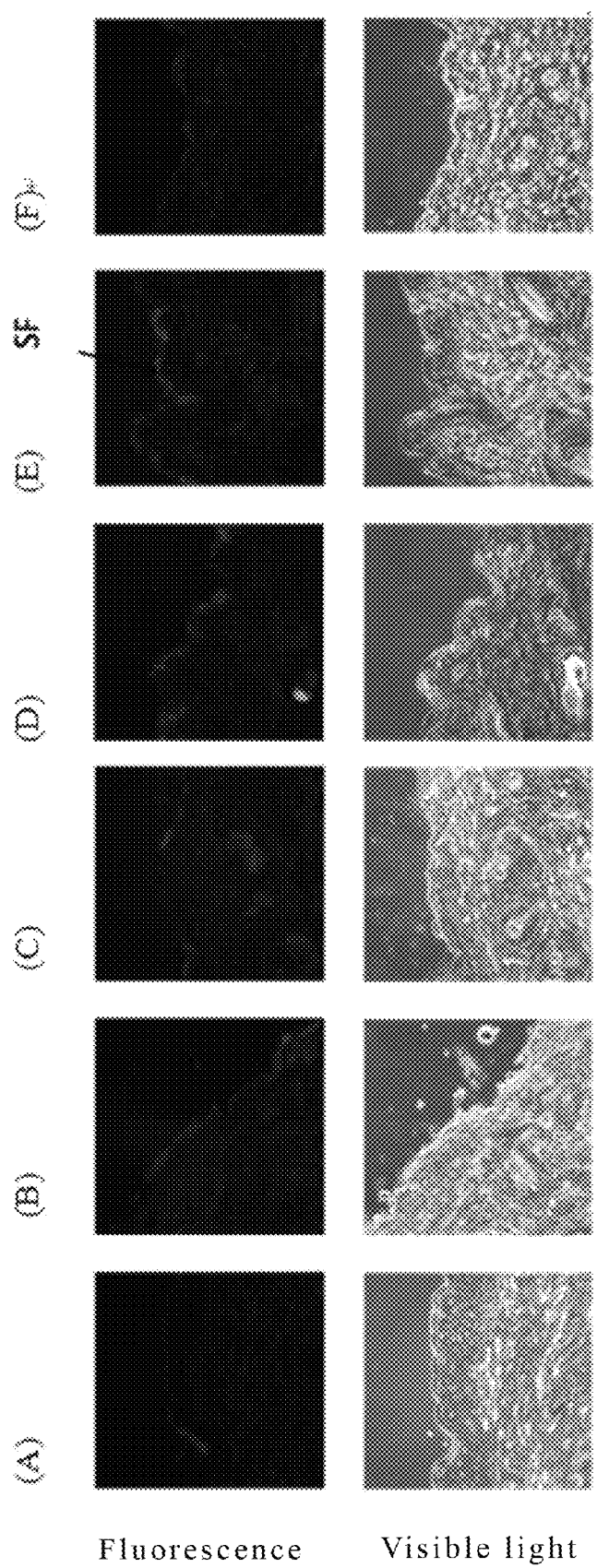
FIG. 7 shows the effect of surfactin on skin absorption of dexamethasone; two groups were tested, in the control group, 100 μl of PBS (pH=7.4) was mixed with fluorescein isothiocyanate (FITC)-labeled dexamethasone before added to 1 cm2 sterile cotton and affixed to the back of the mice; in the experimental group, FITC-labeled dexamethasone was mixed with 0, 0.2, 0.5, 1, 2 and 5% surfactin; the intensity of fluoresce was measured by using a confocal microscope.

From FIG. 7, surfactin enhances skin penetration of dexamethasone; observing the intensity of the fluorescence can estimate the amount of dexamethasone penetrated through the skin; the higher the intensity of the fluorescence, the more the dexamethasone absorption of the skin; FIGS. 7(B), (C), (D) and (E) all show more fluorescence than FIG. 7 (A), indicating 0.2, 0.5, 1 and 2% surfactin can enhance skin penetration of dexamethasone.

3. Surfactin Enhances Skin Absorption of the Moisturizing Factor Hyaluronic Acid (HA)

Figure 8:
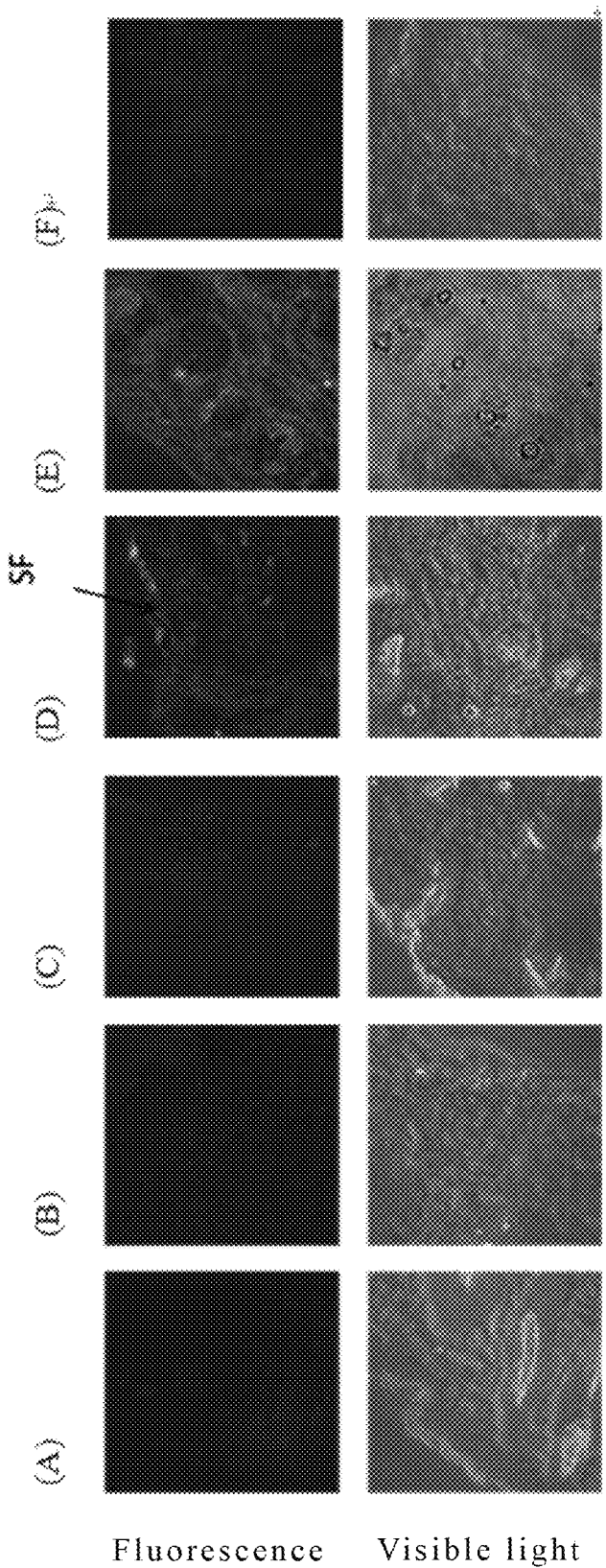
FIG. 8 shows the effect of surfactin on skin absorption of hyaluronic acid (HA); two groups were tested, in the control group, 100 μl of PBS (pH=7.4) was mixed with fluorescein isothiocyanate (FITC)-labeled HA before added to 1 cm2 sterile cotton and affixed to the back of the mice; in the experimental group, FITC-labeled HA was mixed with 0, 0.2, 0.5, 1, 2 and 5% surfactin for 1 hour; the intensity of fluoresce was measured by using a confocal microscope.

Based on FIG. 8, surfactin can increase hyaluronic acid (HA) absorption by the skin; the higher the intensity of the fluorescence, the more the HA absorption of the skin; FIG. 8(A) shows the highest fluorescence intensity, indicating 1% surfactin has the best effect on enhancing skin absorption of the moisturizing factor HA.

4. Surfactin Enhances Skin Absorption of the Moisturizing Factor Gamma-Polyglutamic Acid (γ-GPA)

Figure 9:
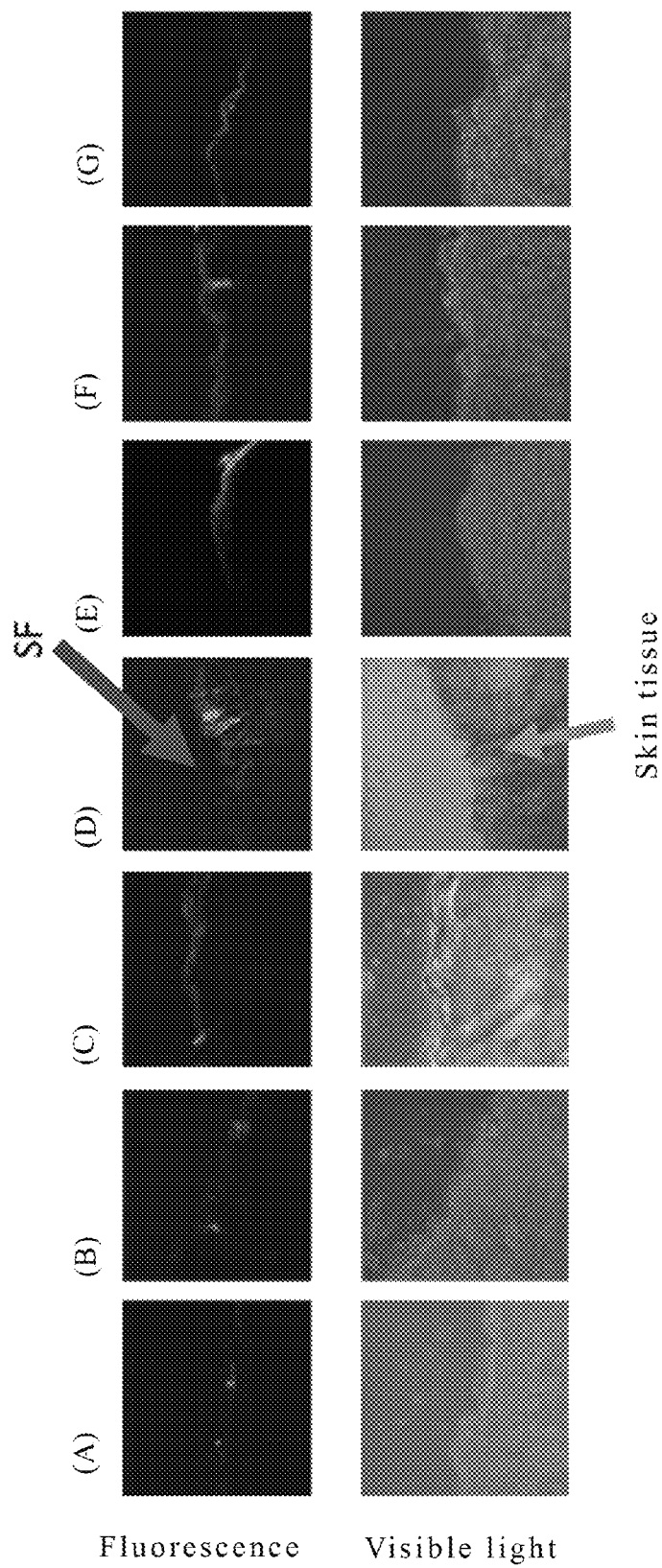
FIG. 9 Shows the effect of surfactin on skin absorption of poly-γ-glutamic acid (γ-GPA); two groups were tested, in the control group, 100 μl of PBS (pH=7.4) was mixed with fluorescein isothiocyanate (FITC)-labeled γ-GPA before added to 1 cm2 sterile cotton and affixed to the back of the mice; in the experimental group, FITC-labeled γ-GPA was mixed with 0%, 1%, 2%, 5%, 10%, 15% and 20% surfactin for 1 hour; the intensity of fluoresce was measured by using a confocal microscope.

From FIG. 9, surfactin can enhance skin absorption of γ-GPA; the higher the intensity of the fluorescence, the more the γ-GPA absorption of the skin; FIGS. 9 (B), (C), (D), (E), (F) and (G) all showed more fluorescence than the control group (A); indicating 1, 2, 5, 10, 15 and 20% surfactin can all increase skin absorption of γ-GPA.

5. Surfactin Enhances Percutaneous Penetration of Gold-Nanoparticles (2 nm)

Figure 10:
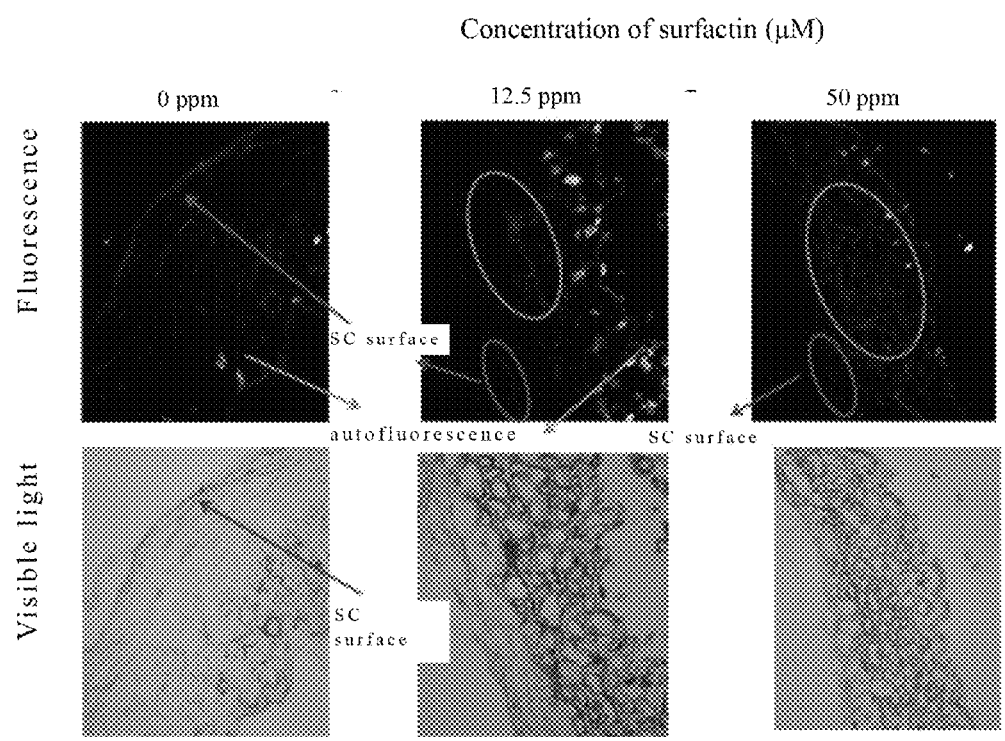
FIG. 10 shows surfactin can enhance skin penetration of gold nanoparticles; the amount of gold nanoparticles was measured by fluorescence microscope; green fluorescence indicates presence of gold nanoparticles, the experiment using gold nanoparticles mixed with surfactin demonstrated more gold nanoparticles were found in the dermis of the mice (BALB/c); the green spot is hair follicles autofluorescence; SC surface: stratum corneum surface.
Figure 11:
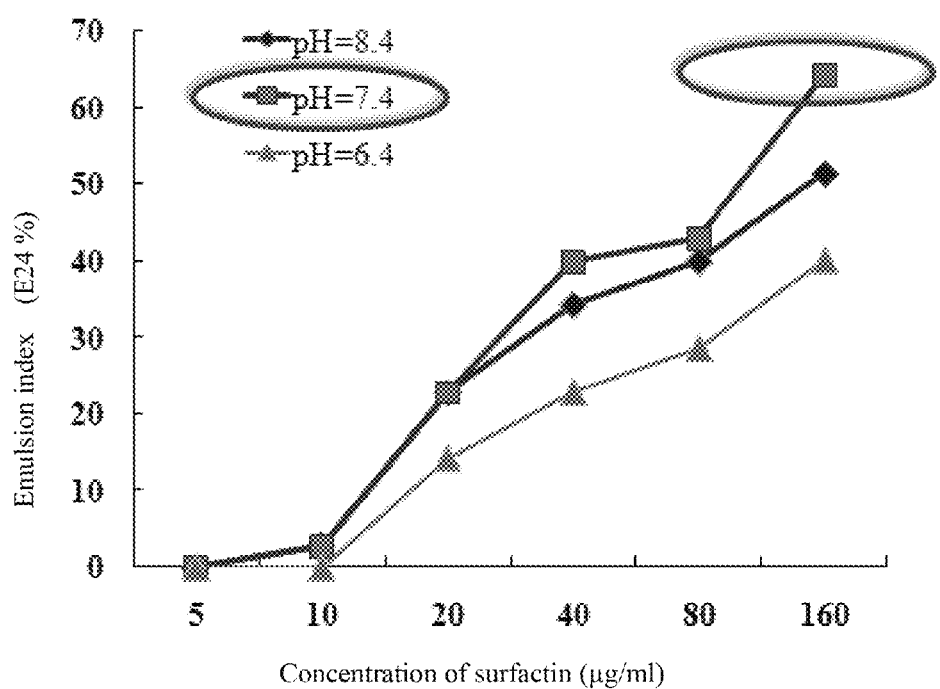
FIG. 11 shows the analysis results of the emulsifying power of surfactin; different concentrations of surfactin was dissolved in buffer solution at various pH (6.4, 7.4 and 8.4) and 2 ml of the dissolved surfactin was added to a test tube containing 3 ml of diesel, followed by vortex for 2 minutes. After incubation at room temperature for 24 hours, emulsification index (E24) was measured.
Figure 12:
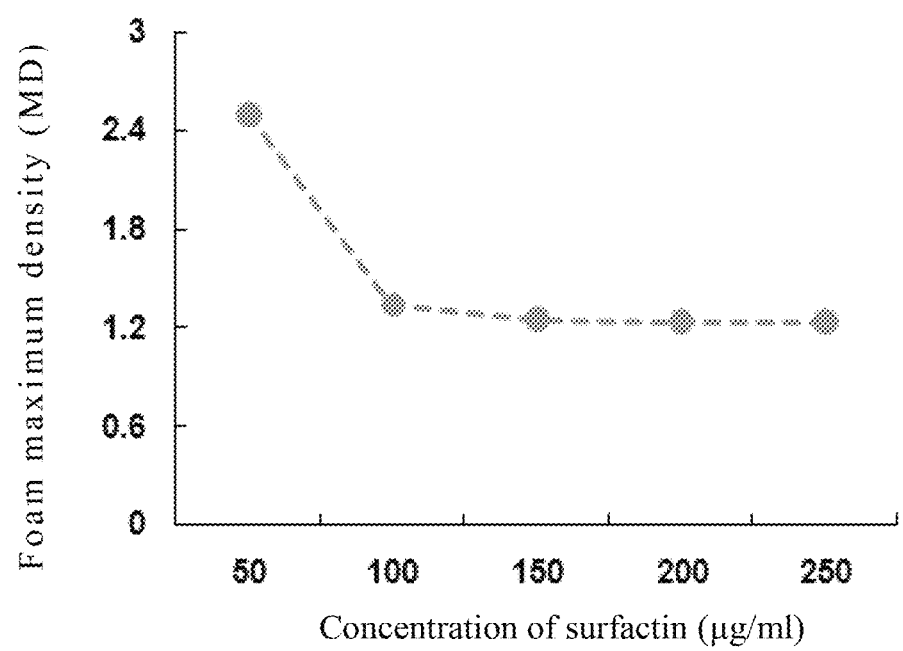
FIG. 12 shows the analysis results of the foaming power of surfactin; crude surfactin were dissolved in buffer solution at pH 7.4 to make different concentrations of surfactin solutions, vortex for 2 minutes followed by incubation for 1 hour. Measure the height of the foam and calculate the foam maximum density (MD).
Figure 13:
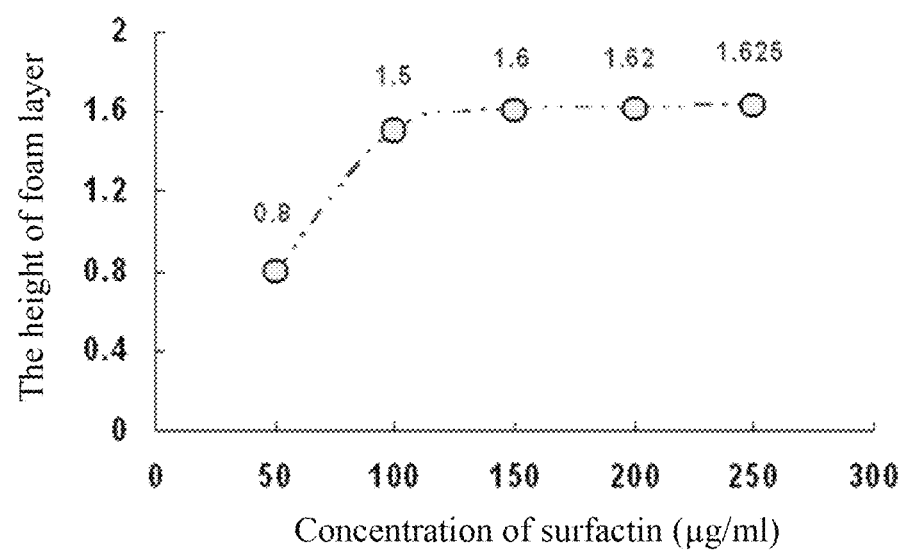
FIG. 13 shows the relationship between the concentration of surfactin and the height of the foam.
Figure 14:
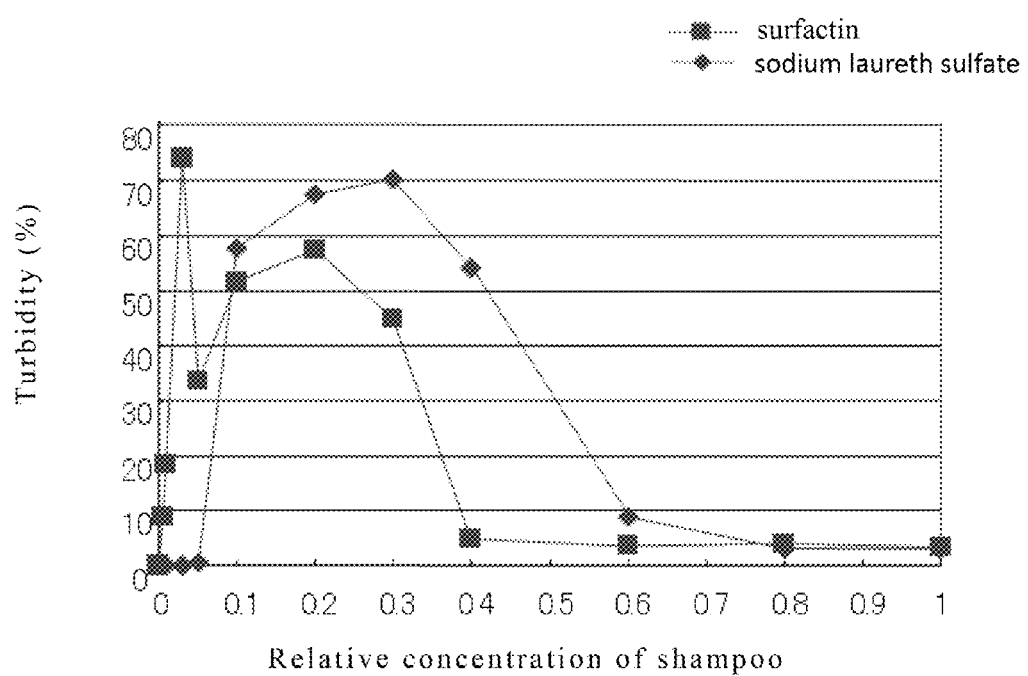
FIG. 14 shows the relationship between the concentration of surfactin and turbidity (%).
Figure 15:
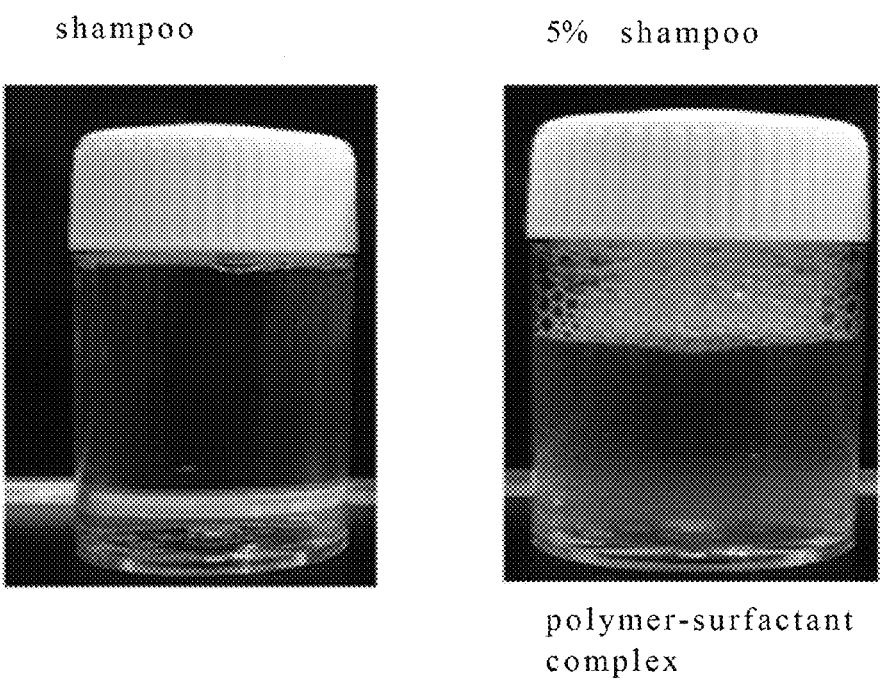
FIG. 15 shows the precipitates in the shampoo containing surfactin after diluted with polymer-surfactant complex.

We applied the mix of gold nanoparticles and surfactin to the skin of mice for a certain period of time and collected the skin for cryosection. Because gold nanoparticles is self-luminous, optical microscope can be used to observe the content of fluorescence of gold nanoparticles in epidermis and dermis of the skin. The results indicated skin care paste obtained by conventional methods is not helpful for gold nanoparticle absorption by the skin due to its internal gel-mass like or gel-bundle like structure and thus gold nanoparticles were only found in the epidermis. On the other hand, addition of 12.5 ppm surfactin can significantly enhance the percutaneous absorption of gold nanoparticles (FIG. 10).

According to the above results, surfactin of the invention can replace chemically synthesized surfactants and be applied widely in TDDA systems.

EXAMPLE 6

Analysis of the Emulsifying Power of Surfactin

The emulsifying power is one of the important indicator of surfactants, and present invention utilized the method published by Cooper et. al to measure the emulsification index of surfactants in diesel. Different concentrations of crude surfactin was dissolved in buffer solutions at pH 6.4, 7.4 and 8.4, and 2 ml of the dissolved mixture was added to a test tube containing 3 ml of diesel, vortex for 2 minutes and incubate at room temperature for 24 hours before measurement. The ration of height of the emulsifying phase and the total height of the solution multiplied by 100% will give the emulsification index of the test solution. The emulsifying power of oil products is represented as the emulsification index ($E_{24}$), wherein the equation of $E_{24}$ is shown as follows:

$$E_{24}(\%)=(\text{height of the emulsifying phase/total height of solution})\times 100\%.$$

From FIG. 11, surfactin has the best emulsifying power at pH=7.4; moreover, at pH=7.4 and a concentration of 160 μg/m, surfactin has the best emulsifying power.

EXAMPLE 7

Surfactin can be Used as a Foaming Agent

1. Analysis of the Foaming Power

Surfactants are low-foaming agents and present invention examined the foaming property of crude surfactin. The method developed by Razafindralambo et. al was referenced and different concentrations of crude surfactin was dissolved in a buffer solution with a pH at 7.4, vortex for 2 minutes and followed by incubation for 1 hour. The height of the foam was then measured and the foaming power is expressed as foam maximum density (MD) which is obtained by dividing the total height of the liquid by the maximum height of the foam.

2. Surfactin can be Used as a Foaming Agent

Surfactin possess numerous biological properties, including the foaming and emulsifying power of common surfactants (Razafindralambo et al., 1998). The so called foaming effect refers to surfactin exists in the interphase between the gas and liquid phase and vigorous shaking allows surfactants to trap the air and form a thin film with air inside (Halling, 1981). The present invention examined whether the surfactin produced by *Bacillus subtilis* TH has the activity to make foam and the results indicated addition of more than 150 μg of surfactin to buffer solution did not reduce the MD value with the minimum at 1.23 (see FIG. 12); this may due to the concentration of surfactin added to the de-ionized water has reached the critical micelle concentration (CMC) and surfactin forms micelles and only monomers in the solution. FIG. 13 shows the relationship between the concentration of surfactin and the height of foam. Razafindralambo et. al suggested that the MD value of surfactin can be as low as 0.10 and surfactin presents better foaming effect when compared with ituirn A; therefore, the structure may play an important role in foaming properties. Surfactin belongs to the anionic surfactants and its fatty acid carbon chain is shorter, while ituirn A is a non-ionic surfactant with a longer fatty acid chain (Razafindralambo, et al., 1998). The surfactin produced by *Bacillus subtilis* TH possess the foaming power and be used in making personal skin care products such as detergents, shampoos, and hand wash gel.

EXAMPLE 8

Surfactin as a Smoothing Agent

Surfactin shows good sense of smooth during flushing; however, at low concentration, corecervate may occur.

1. Surfactin can reduce turbidity (1) Adjust the relative concentration of the shampoo to 0.01-1.0

Relative concentration=shampoo liquid (g)/(shampoo liquid (g)+water (g))

(2) Measure the transmittance rate (%, temperature at 40° C.) of the 420 ml solution (1) and the turbidity is represented as =100−transmittance rate (%)

Based on FIG. 14, when compared with the common emulsifier used in detergents, sodium laureth sulfate, surfactin of the present invention can further reduce the turbidity of the shampoo and increase the sense of smooth.

2. Surfactin Will Form Corecervate

During flushing, surfactin shows excellent sense of smooth; however, corecervate will occur at low concentrations.

From FIG. 15, after diluted with the polymer-surfactant complex—i.e. corecervate, shampoo containing surfactin will form precipitates and thus reduces the friction sensitivity and increases the sense of smooth.

The foregoing detailed description of the invention and the specific examples are provided herein for the purpose of illustration only, and the invention is not limited to the preferred embodiments shown. It should be understood that any changes or modifications within the spirit of the invention shall be included in the scope of present invention.

The invention claimed is:

1. A method for an anti-aging treatment comprising:
administering a cosmetic composition to a subject in need thereof, wherein the cosmetic composition comprises surfactin in a concentration between 25-100 μm, and pharmaceutically acceptable vehicles, excipients, diluents or adjuvants,
wherein the cosmetic composition performs an antiaging effect via enhancement of sirtuin.

2. The method as recited in claim 1, wherein the surfactin is a cycloaliphatic peptide comprising a hepapeptide (L)Glu-(L)Leu-(D)Leu-(L)Val-(L)Asp-(D)Leu-(L)Leu linked to a β-hydroxy fatty acid, and the distribution of the fatty acids at the fatty acid end of the surfactin are as follows:
(1) iso-C13>3%;
(2) C13>0.65%;
(3) iso-C14>17%;
(4) C14<41%; and
(5) iso-C15<11%.

3. The method as recited in claim 2, wherein the distribution of the fatty acids at the fatty acid end of the surfactin are as follows:
(1) iso-C13>10%;
(2) C13>25%;
(3) iso-C14>35%;
(4) C14<25%; and
(5) iso-C15<3%.

4. The method as recited in claim 3, wherein the distribution of the fatty acids at the fatty acid end of the surfactin are as follows: (1) iso-C13=11%; (2) C13=26%; (3) iso-C14=37%; (4) C14=24%; and (5) iso-C15=2%.

5. The method as recited in claim 1, wherein the molecular weight of the surfactin is 1022 or 1036 Da.

6. The method as recited in claim 1, wherein the surfactin comprises its isomers.

7. The method as recited in claim 1, wherein the anti-aging cosmetic composition further comprises at least one of the following ingredients: alcohols, esters, complex polysaccharides, nut oils, and vitamins.

8. The method as recited in claim 7, wherein the alcohol comprises at least one of the following: C16-18 alcohols, butanediol, pentanediol, octanediol, glycerin, hexadecanol, stearyl alcohol, 1-Docosanol and propylene glycol.

9. The method as recited in claim 7, wherein the esters comprise at least one of the following: OLIVEM 1000, glycerol monostearate (GSM), isopropyl myristate (IPM), isopropyl palmitate (IPP) and triglycerides.

10. The method as recited in claim 7, wherein the complex polysaccharides comprise at least one of the following: xanthan gum, Tremella fuciforinis polysaccharides, dextran polysaccharides, and Folium sennae seed polysaccharides.

11. The method as recited in claim 7, wherein the nut oil comprises at least one of the following: Argan oil, Kukui nut oil, avocado oil, wheat germ oil, and olive oil.

12. The method as recited in claim 7, wherein the vitamins comprise at least one of the following: vitamin A, vitamin B, vitamin C, vitamin E, vitamin F, and vitamin K.

13. The method as recited in claim 1, wherein the anti-aging cosmetic composition is used to promote fibroblast proliferation, collagen production or sertuin 1 gene expression.

14. The method as recited in claim 1, wherein the anti-aging cosmetic composition is used to prevent photoaging induced by UV light or anti-oxidation.

15. The method as recited in claim 1, wherein the anti-aging cosmetic composition is used to inhibit matrix metallopeptidase.

16. The method as recited in claim 15, wherein the matrix metallopeptidase is matrix metallopeptidase 9.

17. The method as recited in claim 1, wherein the cosmetic composition comprises surfactin in a concentration between 50-75 μm, and pharmaceutically acceptable vehicles, excipients, diluents, or adjuvants.

* * * * *